United States Patent [19]

Walworth

[11] 3,970,754

[45] July 20, 1976

[54] 1,2-DIALKYL-3(OR 3,5)-N-HETEROCYCLIC PYRAZOLIUM SALTS OF DERIVATIVES THEREOF AS FUNGICIDAL AGENTS

[75] Inventor: Bryant Leonidas Walworth, Pennington, N.J.

[73] Assignee: American Cyanamid Company, Stamford, Conn.

[22] Filed: Mar. 10, 1975

[21] Appl. No.: 556,748

[52] U.S. Cl.................................. 424/267; 424/273
[51] Int. Cl.² ......................................... A01N 9/22
[58] Field of Search ................................... 424/267

[56] References Cited
OTHER PUBLICATIONS

Chemical Abstracts, vol. 79 (1973), p. 92210a.

*Primary Examiner*—V. D. Turner
*Attorney, Agent, or Firm*—Harry H. Kline

[57] ABSTRACT

There is provided a method for controlling fungi with a fungicidally effective amount of a 1,2-dialkyl-3(or 3,5)-N-heterocyclic pyrazolium salt. There is also provided a method for protecting living plants from attack by fungi through the application to the foliage of said plants of a fungicidally effective amount of such pyrazolium salt compounds.

11 Claims, No Drawings

1,2-DIALKYL-3(OR 3,5)-N-HETEROCYCLIC PYRAZOLIUM SALTS OF DERIVATIVES THEREOF AS FUNGICIDAL AGENTS

The present invention relates to a method for controlling fungi with pyrazolium compounds which have a nitrogen containing heterocyclic group either in the 3 position, or in the 5 position or in the 3 and 5 positions of the pyrazolium ring and are represented by a formula:

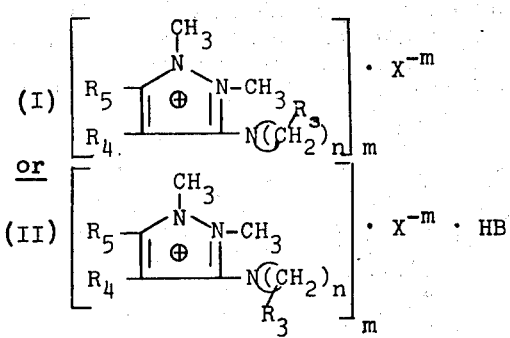

wherein $R_3$ is a member selected from the group consisting of hydrogen, methyl, hydroxy and phenyl; $R_4$ represents a member selected from the group consisting of hydrogen or halogen; $R_5$ represents a member selected from the group consisting of phenyl, cyclohexyl and

X represents an anion with a charge of 1 or 2 and preferably 1; n represents an integer selected from 4, 5 and 6; m represents an integer selected from 1 and 2; and HB represents an inorganic or organic acid.

As employed in the present application the term "halogen" is intended to mean fluorine, chlorine, bromine and iodine; however, bromine is preferred.

Illustrative of the anions, represented by X, which are suitable for use in the present invention are, for example, halides such as chloride, bromide or iodide; acetate; sulfate, hydroxide; hydrogen sulfate; methyl sulfate; benzene sulfonate; alkoxy ($C_1$–$C_4$) benzene sulfonate: alkyl ($C_1$–$C_3$) benzene sulfonate, such as, p-toluene sulfonate; nitrate; phosphate; tetrafluoroborate, $(C_6H_5)_4B$; iodate; alkane sulfonate ($C_1$–$C_4$); perchlorate; $Br_3^-$ and $I_3^-$.

With regard to the pyrazolium salts of formula (I), it is to be understood that certain multivalent anions such as sulfate, phosphate, and the like may have associated with them a cation in addition to the pyrazolium, as for example a proton or an alkali metal or alkaline earth metal. For simplicity, such anions are characterized as being unionized, although they probably are further ionized in fact. Typical representations are: $NaSO_4^-$, $KPO_4^=$, $MgPO_4^-$, $HSO_4^-$, and $NaHPO_4^-$.

Illustrative of the acid residue, identified in formula (II) above as . HB, which is suitable for use in the present invention are (a) inorganic acids, such as HCl, HI, HBr, $HClO_4$, $H_2SO_4$, $HNO_3$ and $H_3PO_4$ and (b) organic acids, such as $CH_3SO_3H$,

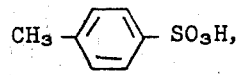

$ClCH_2COOH$, and other organic acids of sufficient acid strength to form stable salts with

group.

Preferred compounds useful for the practice of the method of this invention are represented by above-identified formulas (I) and (II), respectively, wherein $R_3$ is hydrogen or methyl; $R_4$ is hydrogen, $R_5$ is phenyl, or cyclohexyl; n is 5; m is 1 or 2; and X is an anion with a charge of 1 or 2.

Exemplary of the effective compounds useful in the present invention are:

1,2-Dimethyl-3-phenyl-5-piperidinopyrazolium iodide, hydroiodide, 1,2-Dimethyl-3-phenyl-5-piperidinopyrazolium perchlorate, perchloric acid salt, 1,2-Dimethyl-3-phenyl-5-(1-pyrrolidinyl)pyrazolium methyl sulfate, 3-(Hexahydro-1H-azepin-1-yl)-1,2-dimethyl-5-phenylpyrazolium iodide, 1,2-Dimethyl-3-(4-methylpiperidino)-5-phenylpyrazolium iodide, 1,2-Dimethyl-3-(2-methylpiperidino)-5-phenyl-pyrazolium iodide, 1,2-Dimethyl-3-(3-methylpiperidino)-5-phenylpyrazolium iodide, 4-Bromo-1,2-dimethyl-3,5-dipiperidinopyrazolium bromide, hydrobromide, 4-Bromo-1,2-dimethyl-3,5-dipiperidinopyrazolium perchlorate, perchloric acid salt, 1,2-Dimethyl-3,5-dipiperidinopyrazolium bromide, nitric acid salt, 1,2-Dimethyl-3,5-dipiperidinopyrazolium perchlorate, 1,2-Dimethyl-3-(3-methylpiperidino)-5-phenyl-pyrazolium perchlorate, 1,2-Dimethyl-3-(3-methylpiperidino)-5-phenyl-pyrazolium bromide, 1,2-Dimethyl-3-(3-methylpiperidino)-5-phenyl-pyrazolium methyl sulfate, 1,2-Dimethyl-3-(3-piperidino)-5-phenylpyrazolium chloride, 1,2-Dimethyl-3-(2-methylpiperidino)-5-phenyl-pyrazolium methyl sulfate, 3-Cyclohexyl-1,2-dimethyl-5-(3-methylpiperidino)-pyrazolium methyl sulfate (and chloride), 1,2-Dimethyl-3-(2-methylpiperidino)-5-phenyl-pyrazolium perchlorate, 1,2-Dimethyl-3-(2-methylpiperidino)-5-phenyl-pyrazolium chloride, hydrochloride, 3-Cyclohexyl-1,2-dimethyl-5-(3-methylpiperidino)-pyrazolium iodide, 3-Cyclohexyl-1,2-dimethyl-5-piperidinopyrazolium iodide, 1,2-Dimethyl-3-(3-hydroxypiperidino)-5-phenyl-pyrazolium iodide, In accordance with the invention, compounds of formula (I) defined above can be synthesized from an intermediate (IV), defined below, by reaction of the intermediate 3-halopyrazolium compounds (IV) with a saturated azaheterocycle or a saturated N-containing heterocycle (III) hereinbelow defined within a temperature range of from about 20°C. to about 100°C. In this reaction it is necessary to include either two moles of the azaheterocycle, one as a base acceptor, or to use one mole of azaheterocycle and one mole of an organic or inorganic base acceptor. In practice tertiary amines, such as trimethylamine, triethylamine, pyridine or quinoline as well as inorganic bases, such as sodium bicarbonate, sodium carbonate and the like can be employed.

The reaction is graphically illustrated as "Method A" as follows:

either by exchange chromatography (Method A) on an appropriately modified Dowex 1-X8 base anion exchanged or in some cases by the addition of a concentrated solution of an acid salt (Method A salt) e.g. utilizing sodium iodide, sodium tetrafluoroborate, or sodium perchlorate [or 10% aqueous perchloric acid (Method A acid)], thereby causing the water insoluble salt to precipitate. When an acid is used as, for instance, perchloric acid, not only does ion exchange occur, but there also may occur the formation of a perchlorate salt of the azaheterocyclic group.

Purification of a formula (I) compound above can be effected by dissolving said compound in water, excepting the water insoluble salts, such as perchlorate or iodide, and washing the aqueous layer with ether, discarding the ether layer, then extracting the same with chloroform or methylene chloride. Product (I) may

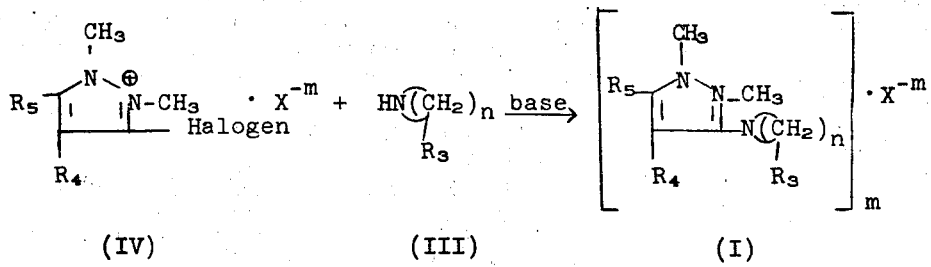

(IV)    (III)    (I)

where $R_3$, $R_4$, $R_5$, $m$, $n$ and X are each as defined above. This reaction involves displacement of a halogen by a azaheterocycle group. Additionally a variety of inert solvents such as methanol, ethanol, propanol, dimethylformamide (DMF), acetone, acetonitrile or the like can be utilized during reaction.

A limitation to this procedure is reaction temperature and time. Heating the (IV) compound with an excess of azaheterocycle, especially at temperatures above 100°C. over an extended time, causes increasing dealkylation of the pyrazolium compound (I) to the pyrazole. Thus, to prevent dealkylation, the preferred reaction temperature is 80°C., or less, and preferably 40°C. to 80°C.

The counter ion X employed in the Method A may be any of those listed, although methyl sulfate, iodide, bromide, chloride, perchlorate, and tetrafluoroborate are generally preferred. The product identified by formula (I) may be prepared with a particular anion X either by reacting compound IV containing the required anion X or by alternative procedures outlined below. For example, the anion of (I) may be replaced then be precipitated from the chlorinated hydrocarbon by the addition of diethyl ether.

The preparation of 3-halopyrazolium compound (IV) employed in Method A can be accomplished by the stepwise reactions involving: (1) a benzoyl acetic acid ester or a cycloalkanoyl acetic acid ester (V) defined more particularly hereinbelow with methyl hydrazine to yield a 3-pyrazolinones (VI), (2) halogenation of said pyrazolinone (VI) with phosphorus oxyhalide to yield the corresponding 3-halopyrazole (VII), and (3) methylation of said 3-halopyrazole (VII) to yield a 3-halopyrazolium compound (IV). Conversion of the formula (IV) 3-halopyrazolum salt to the formula (I) pyrazolium salt containing, the 3-nitrogen heterocyclic group is readily achieved by reaction of the halopyrazolium salt with an azaheterocycle in the presence of base, as described above.

The four reaction steps are graphically illustrated below with phosphorus oxychloride used to represent the oxyhalide employed as the halogenation reagent of the pyrazolinone (VI).

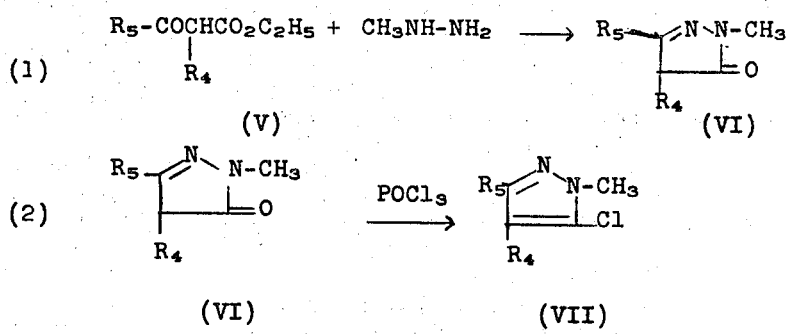

(3) 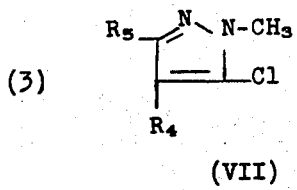 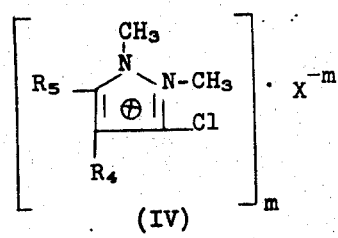

(4) 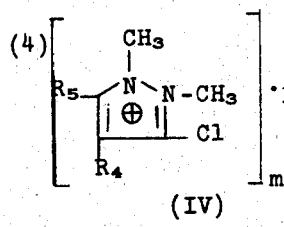 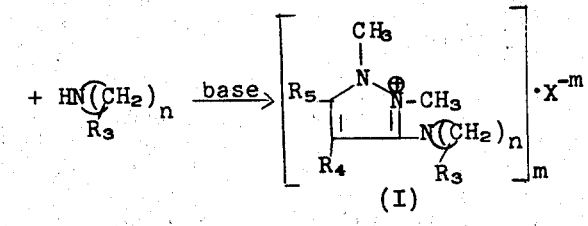

where $R_3$, $R_4$, $R_5$, $m$ and $n$ are each as defined above.

The methylation reaction in Step 3 above is preferably conducted in the presence of a solvent, such as xylene, toluene, benzene, 1,2-dichloroethane or the like. Alternatively, it may be conducted to the exclusion of a solvent using solely the halopyrazole (VII) reactant and the alkylating agent.

Illustrative methylation reagents include, methyl sulfate, methyl halides, methyl hydrogen sulfate, methyl toluene sulfonate and the like.

In general, the halopyrazole and methylating reagent combine on an equimolar basis. However, it is a good practice to employ an excess of the methylating agent. Optimum reaction conditions for effecting the methylations will vary depending on the reactants employed. Reaction is effected by combining the methylating agent and an halopyrazole usually in the presence of a solvent. The reaction mixture is heated until the reaction occurs. Where the methylating reagents employed are volatile, such as methyl chloride, the reaction is preferably conducted in a sealed vessel under pressure, to avoid loss of the reactants. The quaternization of the formula (IV) 3-halopyrazolium compound is accomplished by utilizing a methylating agent, such as dimethylsulfate, methyl chloride, methyl iodide or other such agent, alone or admixed with a solvent.

The preparation of formula (IV) 3-halopyrazolium compounds where $R_4$ is halogen, can be accomplished by direct halogenation of the 1-methyl-3-halopyrazole (VII) in acetic acid.

Compounds containing 3,5-disubstituted azaheterocyclic substituents (IX) can be prepared by a process, hereinafter referred to as Method B. This method involves the reaction of a 3,5-dihalopyrazolium compound with an azaheterocycle; both 3 and 5-dihalogens react rapidly at ambient temperatures up to 80°C. However, under these conditions, the substituent in the 4-position, even a 4-halogen, is unreactive to an azaheterocycle. The reaction is preferably conducted in the presence of a base and an aprotic solvent such as xylene, toluene, benzene or the like. This reaction "Method B" is graphically illustrated as follows:

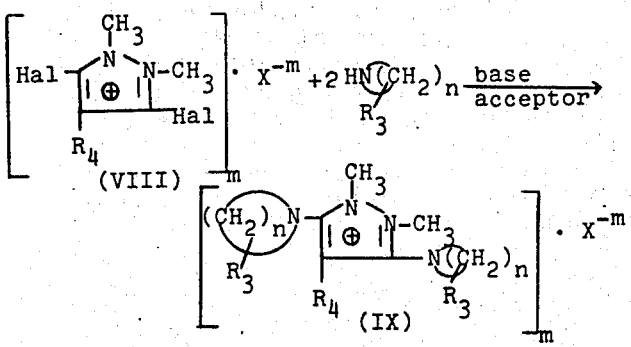

where $R_3$, $R_4$, $m$ and $n$ are each as defined above.

In practice it has been found that formula (X) 3,5-diazaheterocyclylaminopyrazolium compounds where $R_4$ is hydrogen, can be most advantageously prepared from formula (IX) 3,5-diazeheterocyclylamino-4-halopyrazolium compounds by a dehydrohalogenation process, hereinafter referred to as "Method C". The process involves the reaction of a 3,5-diazaheterocyclylamino-4-halopyrazolium salt (XI) with hydrogen, in the presence of a strong base such as an alkali metal alkoxide (e.g. sodium methoxide, sodium ethoxide or potassium t-butoxide) and a catalyst such as palladium or platinum on carbon. The reaction is preferably conducted at a temperature between about 20°C. and 40°C. and may be illustrated as follows:

Method C

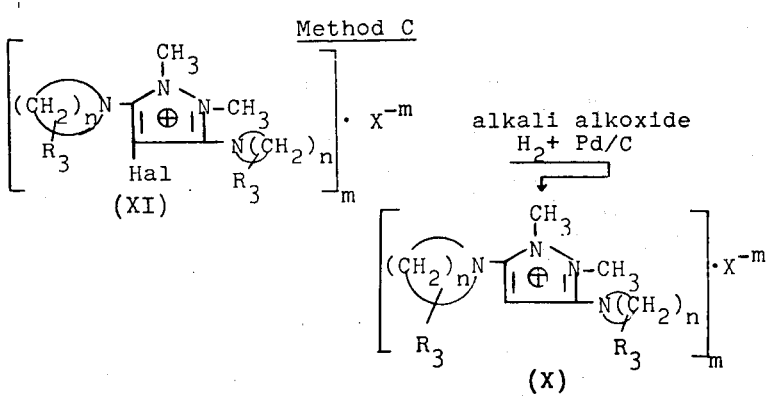

As noted above, the hereinabove recited compounds are effective for the control of fungi which infect many living plants. They are particularly effective for controlling powdery mildew, especially on grains such as barley, corn, sorghum and wheat, on vines such as cucumbers, grapes and pumpkin and on fruit and nut trees such as apples, pears and pecans. However, they are also effective for controlling fungi which are the causative agents for other diseases such as rice blast, and apple scab.

In utilizing the above-identified pyrazolium salts for protecting plants from pathogenic fungi, it has been found most advantageous to apply the compounds herein foliage of the plant in the form of a liquid, preferably aqueous, spray. Solutions or suspensions containing from about 100 to 5600 ppm, and preferably 100 to 1000 ppm of the pyrazolium salt, are generally highly effective for this use.

For application as liquid sprays, said compounds are generally prepared as emulsifiable concentrates, wettable powders, or water miscible concentrates which are diluted with water or other suitable polar solvents, and then applied as a dilute spray. Generally such sprays are applied at the volume rate of about 938 liters to 1877 liters/hectare (l/ha) or about 100 or 200 gal per acre. It is, of course, obvious that smaller or larger volumes of liquid spray may be employed, eg., 400 to 4000 l/ha may be used depending on a variety of factors including the type of crop, the plant spacing and the amount of foliage per plant being treated.

Wettable powder formulations can be prepared by grinding together about 25% to 95% by weight of the pyrazolium salt and about 75% to 5% by weight of a solid diluent such as attapulgite, kaolin, bentonite, diatomaceous earth, silica, talc, fullers earth or the like. To this mixture is added about 1% to 5% by weight of a dispersing agent, such as the calcium salt of a polymerized alkyl aryl sulfonic acid, sodium lignosulfonate, or sodium salt of condensed naphthalene sulfonic acid, and about 1% to 5% by weight of a surfactant, such as polyoxyethylated vegetable oil, alkyl phenoxy polyoxyethylene ethanol, sodium alkyl naphthalene sulfonate, is also blended with the formulation.

The water-miscible concentrates are prepared by dissolving from 15% to 70% by weight of the compound in 85% to 30% by weight of a water-miscible solvent, such as water itself or another polar water-miscible solvent, such as 2-methoxy ethanol, methanol, propylene glycol, diethylene glycol, diethylene glycol monoethyl ether, formamide, and methylformamide. Application of the material is made by adding a predetermined quantity of the water-miscible concentrate to a spray tank and applying as such or in combination with additional suitable diluent, such as a further quantity of water or one of the above polar solvents mentioned above.

The performance of the product in the above formulations, which are applied as liquid sprays, is improved by adding a surfactant or blend of surfactants thereto. Conventional nonionic surfactants are preferred and the surfactants are preferably added to the formulation or the spray tank at the rate of 0.1% to 5% by volume to provide good wetting of the spray solution on plant foliage.

Suitable nonionic surfactants include alkyl polyoxyethylene ethers, polyoxyethylene (20) sorbitan monolaurate, polyoxyethylene (20) sorbitan monooleate, alkylarylpolyglcol ethers, alkyl phenol ethoxylates, trimethyl nonyl polyethylene glycol ethers, alkyl phenol ethylene oxide condensates, octyl phenoxy polyethoxy ethanols, nonylphenyl polyethylene glycol ethers, condensates of polyoxy ethylenes, polyoxy propylenes, aliphatic polyethers, aliphatic polyesters, alkylarly poloxyethylene glycols, and the like. Especially preferred nonionic surfactants having a hydrophilic-lipophilic balance (HLB) of from 11 to 16. This conventional surfactant classification test is described, for example, at page 232 et seq of *Emulsion Theory and Practice* by Paul Becker, Rheinholt Publishing Corporation, second edition (1965); also available as No. 162 in the American Chemical Society's Monograph Series.

Generally, the plants which are to protected against attack from fungal organisms are sprayed to run off with solutions or suspensions of the above-identified compounds. In practice it has been found that solutions or suspensions containing from about 100 to 5600 ppm of the compounds herein and preferably 100 to 1000 ppm of such compounds afforded the desired protection.

In order to facilitate a further understanding of the invention, the following examples are presented primarily for purposes of illustrating certain more specific details thereof. The invention is not to be deemed limited thereby except as defined in the claims. Unless otherwise noted, the parts are by weight.

EXAMPLE 1

To determine the effectiveness of the 1,2-dialkyl-3(or 3,5)-mono(or di)heterocyclic pyrazolium salts as fungicidal agents, a variety of pathogenic fungi, host plants and acid salts are used in the following tests. Pathogens, host plants, the method of testing, the rating system used, and the data obtained are set forth below.

Pathogens:
*Piricularia oryzae* Cavara, the rice blast pathogen.
*Venturia inaequalis* (Cke.) Wint. which causes apple scab.
*Erysiphe cichoracearum* DC, the cause of powdery mildew on cucurbits.
*Podosphaera leucotricha* (E. & E.) Salm., the cause of powdery mildew of apples and pears.
*Erysiphe graminis* f. sp. tritici the cause of powdery mildew on wheat.
*Erysiphe graminis* f. sp. hordei the cause of powdery mildew on barley.

Host Plants:
Rice (*Oryza sativa*) Cv. Nato)
Cucumber (*Cucumis sativus*) (Cv. Marketer)
Apple (*Malus sylvestris*) (Seedling)
Wheat (*Triticum aestivum* Cv. Bonanza)
Barley (*Hordeum vulgare* Cv. Larker)

Plants are individually grown in 5.08 cm peat squares and assembled in 7.62 cm. × 25.4 cm. pressed fibre containers the week prior to spraying. With exception of rice, barley, and wheat, a single specimen of each species is used. A separate container is used for those plants in the mildew evaluation. The complete test system is shown below.

| Series 1 | | Series 2 |
| --- | --- | --- |
| Rice: | Rice Blast | Apple: | Powdery Mildew |
| Apple: | Apple Scab | Cucumber: | Powdery Mildew |
| | | Wheat: | Powdery Mildew |
| | | Barley: | Powdery Mildew |

Spray solutions are prepared at a final concentration of 100 ppm or 500 ppm in 50 ml of 50% aqueous acetone. Acetone is added to solubilize the test compound and solutions made to final volume with deionized water.

Two containers, one each from Series 1 and 2 (see above), are sprayed simultaneously on a turntable with 50 ml of the test solution. Spray is provided by two fixed spraying nozzles mounted to deliver vertical and horizontal solid cone spray patterns. Immediately thereafter, all plants are returned to the greenhouse to permit the deposit to dry. Plants of Series 1 and 2 are separately inoculated. Plants in Series 1 are inoculated with conidial suspensions of the respective pathogens using a paint sprayer operated under 4–6 psig and, immediately, are transferred to a controlled temperature/humidity cabinet (ambient temperature, RH~95%). Plants in Series 2 are dusted with respective powdery mildew conidia and then removed to the controlled environment plant culture room (10 hours light, ~22°C., RH 45%) to await disease development. Plants in Series 1 are held 4 days in the cabinet, then transferred to the greenhouse to await disease expression.

Performance Rating

All plants are rated for disease severity on a scale of 1 to 7 (clean to kill), as described below:

| Rating | Description |
| --- | --- |
| 1 | Clean |
| 2 | Trace disease |
| 3 | Slight disease |
| 4 | Moderate disease |
| 5 | Heavy disease |
| 6 | Severe disease |
| 7 | Kill |

In the tables hereinbelow presented, the numerical rating is used for clarity. Data obtained are reported in Tables I and II below. The ratings reported represent data obtained from one or more individual tests. Where more than one test has been conducted, the ratings are averaged and reported as a single value rating. For each table, there is also provided a rating value for the checks employed and a rating range for acceptable disease control. It is, of course, obvious that the lower the value, the more effective the disease control.

Table I

| Disease Severity of Plants Sprayed to Run-off with Indicated Rates (ppm) | | | | |
| --- | --- | --- | --- | --- |
| Compound | Rice Blast | | Apple Scab | |
| | 500 | 100 | 500 | 100 |
| Acceptable Level of Control | 1–4 | | 1–4 | |
| Untreated Controls Average Rating | 5.1 | | 5.4 | |
| 1,2-Dimethyl-3-phenyl-5-piperidino-pyrazolium iodide | | | 3.0 | |
| 1,2-Dimethyl-3-phenyl-5-(1-pyrrolidinyl)-pyrazolium methyl sulfate | | | 4.0 | |
| 1,2-Dimethyl-3-(4-methylpiperidino)-5-phenylpyrazolium iodide | | | 4.0 | |
| 1,2-Dimethyl-3-(3-methylpiperidino)-5-phenylpyrazolium bromide | | | 4.0 | |
| 1,2-Dimethyl-3-(3-methylpiperidino)-5-phenylpyrazolium perchlorate | | | 3.5 | |
| 1,2-Dimethyl-3-(3-methylpiperidino)-5-phenylpyrazolium methyl sulfate | | | 4.0 | |
| 1,2-Dimethyl-3-(3-methylpiperidino)-5-phenylpyrazolium chloride | 3.0 | | 4.0 | |
| 1,2-Dimethyl-3-(2-methylpiperidino)-5-phenylpyrazolium perchlorate | 4.0 | | | |
| 3-Cyclohexyl-1,2-dimethyl-5-(3-methylpiperidino)pyrazolium methyl sulfate (and chloride) | | | | |
| 3-Cyclohexyl-1,2-dimethyl-5-(3-methylpiperidino)pyrazolium iodide | | | 2.0 | 3.0 |
| 3-Cyclohexyl-1,2-dimethyl-5-piperidino-pyrazolium iodide | 4.0 | | 2.0 | 3.0 |
| 4-Bromo-1,2-dimethyl-5-(3-methylpiperidino)-3-phenylpyrazolium iodide | | | | 3.0 |
| 4-Bromo-1,2-dimethyl-5-(4-methylpiperidino)-3-phenylpyrazolium iodide | | | 2.0 | 3.0 |
| 4-Bromo-1,2-dimethyl-3-phenyl-5-piperidino-pyrazolium iodide | | | 4.0 | 4.0 |
| 4-Bromo-1,2-dimethyl-3-(2-methylpiperidino)-5-phenylpyrazolium perchlorate | | | 1.0 | |
| 3-(3-Hydroxypiperidino)-1,2-dimethyl-5-phenylpyrazolium perchlorate | | | 1.0 | |

Table II

| Disease Severity of Plants Sprayed to Run-off with Indicated Rates (ppm) | | | | | | | | |
| --- | --- | --- | --- | --- | --- | --- | --- | --- |
| Compound | Cucumber Powdery | | Wheat Powdery | | Apple Powdery | | Barley Powdery | |
| | 500 | 100 | 500 | 100 | 500 | 100 | 500 | 100 |
| Acceptable Level of Control | 1–4 | | 1–3 | | 1–3 | | 1–4 | |
| Untreated Controls Average Rating | 6.0 | | 5.9 | | 5.6 | | 5.4 | |
| 1,2-Dimethyl-3-phenyl-5-piperidino-pyrazolium iodide | 4.0 | | 2.3 | 3.0 | 3.3 | 3.5 | 4.0 | 4.0 |
| 3-(Hexahydro-1H-azepin-1-yl)-1,2- | 4.0 | | 3.0 | | 4.0 | | | |

Table II-continued

| Compound | Cucumber Powdery 500 | Cucumber Powdery 100 | Wheat Powdery 500 | Wheat Powdery 100 | Apple Powdery 500 | Apple Powdery 100 | Barley Powdery 500 | Barley Powdery 100 |
|---|---|---|---|---|---|---|---|---|
| Acceptable Level of Control | 1-4 | | 1-3 | | 1-3 | | 1-4 | |
| Untreated Controls Average Rating | 6.0 | | 5.9 | | 5.6 | | 5.4 | |
| dimethyl-5-phenylpyrazolium iodide | | | | | | | | |
| 1,2-Dimethyl-3-(4-methylpiperidino)-5-phenylpyrazolium iodide | 1.0 | | 2.0 | | 3.0 | | | |
| 1,2-Dimethyl-3-(2-methylpiperidino)-5-phenylpyrazolium iodide | | | 2.8 | | | | 3.3 | 4.3 |
| 1,2-Dimethyl-3-(3-methylpiperidino)-5-phenylpyrazolium iodide | | | 1.0 | 4.0 | 3.0 | | 1.0 | 3.0 |
| 1,2-Dimethyl-3-(3-methylpiperidino)-5-phenylpyrazolium bromide | 2.7 | | 2.0 | 2.5 | 3.3 | 2.5 | 2.5 | 4.0 |
| 1,2-Dimethyl-3-(3-methylpiperidino)-5-phenylpyrazolium perchlorate | 4.3 | | 2.3 | | 4.3 | | 3.5 | |
| 1,2-Dimethyl-3-(3-methylpiperidino)-5-phenylpyrazolium methyl sulfate | 3.0 | | | | 4.0 | | | |
| 1,2-Dimethyl-3-(3-methylpiperidino)-5-phenylpyrazolium chloride | | | 1.0 | | 1.0 | | | |
| 1,2-Dimethyl-3-(2-methylpiperidino)-5-phenylpyrazolium chloride hydrochloride | | | 3.3 | | 4.0 | | 3.5 | |
| 1,2-Dimethyl-3-(2-methylpiperidino)-5-phenylpyrazolium perchlorate | 4.0 | | 4.0 | | | | | |
| 1,2-Dimethyl-3-(2-methylpiperidino)-5-phenylpyrazolium methyl sulfate | 4.0 | | | | | | | |
| 3-Cyclohexyl-1,2-dimethyl-5-(3-methylpiperidino)pyrazolium methyl sulfate and chloride | 4.0 | | 1.0 | 3.0 | | 3.0 | 2.0 | 4.0 |
| 3-Cyclohexyl-1,2-dimethyl-5-(3-methylpiperidino)pyrazolium iodide | 1.0 | 4.0 | 2.0 | 4.0 | 4.0 | | 3.0 | 4.0 |
| 3-Cyclohexyl-1,2-dimetyl-5-piperidinopyrazolium iodide | 1.0 | | 2.0 | 4.0 | | | | |
| 4-Bromo-1,2-dimethyl-5-(3-methylpiperidino)-3-phenylpyrazolium iodide | | | 2.0 | 3.0 | | | 2.0 | 3.0 |
| 4-Bromo-1,2-dimethyl-3-phenyl-5-piperidinopyrazolium iodide | | | 3.0 | 4.0 | 4.0 | | 4.0 | |

EXAMPLE 2

The fungicidal activity of the compounds of the present invention is demonstrated in the following tests.

Wheat plants are individually grown in 5.08 cm peat squares and assembled in containers the week prior to spraying.

Spray solutions are prepared at a final concentration of 500 ppm in 50%/50% water/acetone mixtures. The plants are placed on a turntable and sprayed with 50 ml of test solution. Immediately thereafter they are placed on greenhouse benches and permitted to dry. After drying, said treated plants are dusted with powdery mildew spores and the dusted plants are then placed in a constant temperature room (22°C 10 hours light and 45% RH) for from 7 days to 9 days to await disease expression. At the end of the holding period, all plants are examined and rated according to the performance rating system provided below.

Performance Rating

All plants were rated for disease severity on a scale of 1 – 7 (clean - kill), as described in Example I above. Data obtained are reported in Table III below.

Table III

Control of Powdery Mildew on Wheat

| Compound | Rate ppm | Disease Severity |
|---|---|---|
| 1,2-Dimethyl-3-(3-methylpiperidino)-5-phenylpyrazolium chloride | 500 | 1-Clean |
| 1,2-Dimethyl-3-(3-methylpiperidino)-5-phenylpyrazollium perchlorate | 500 | 1-Clean |
| 1,2-Dimethyl-3-(3-methylpiperidino)-5-phenylpyrazolium iodide | 500 | 1-Clean |
| 1,2-Dimethyl-3-(4-methylpiperidino)-5-phenylpyrazolium iodide | 500 | 2-Trace |
| 1,2-Dimethyl-3-(2-methylpiperidino)-5-phenylpyrazolium iodide | 500 | 2-Trace |
| 3-(Hexahydro-1H-azepin-1-yl)-1,2-dimethyl-5-phenylpyrazolium iodide | 500 | 3-Slight |
| 1,2-Dimethyl-3-phenyl-5-piperidinopyrazolium iodide | 500 | 3-Slight |

From these data it is apparent that 1,2-dimethyl-3-(2,3 or 4-methylpiperidino)-5-phenylpyrazolium salts are preferred fungicidal agents effective for the control of powdery mildew on wheat.

The following examples illustrate the preparation of the compounds employed as fungicides herein.

EXAMPLE 3

Preparation of 1-methyl-3-phenyl-2-pyrazolin-5-one

Ethyl benzoylacetate (1,538 g, 8 moles) dissolved in isopropanol (6 l) is placed in a 12 l flask under an atmosphere of nitrogen. Methylhydrazine (410 g, 8.7 moles, 98%) in isopropanol (800 ml) is added with stirring in a dropwise manner to the ethyl benzoylacetate solution prewarmed to about 80°C. During the addition the external heating is removed. Seeding of the reaction mixture with the product at the point of one-third addition of methylhydrazine causes a copious precipitate of product. This procedure eliminates a large exotherm from occurring at a later stage. After the addition is complete, the reaction mixture is held at about 80°C. for 2 hours. Cooling the slurry to 20°C. and filtering off the solid, a yield of 1,131 g (81%) of product after drying with a melting point equal to 211°C. is obtained.

EXAMPLE 4

Preparation of 5-chloro-1-methyl-3phenylpyrazole

To a solution of phosphorous oxychloride (2,015 g, 19 moles) is added solid 1-methyl-3-phenylpyrazolin-5-one (2,073 g, 11.9 moles) with stirring and warming. At 100°C. the mixture becomes homogeneous. The reflux temperature rises from 119°C. to 143°C. over a period of 30 hours. After cooling the mixture is poured into ice and water (8 l) with stirring. After 4 hours the slurry is filtered and the filter cake added to 4 l of water containing 1.5 l of 10% sodium hydroxide solution with stirring. Removal of the solid by filtration followed by a recrystallization from hexane yields 1,523 g of product, having a melting point ranging from 61°C. to 62°C.

EXAMPLE 5

Preparation of 3-chloro-1,2-dimethyl-5-phenylpyrazolium methyl sulfate, utilizing one of two methods

METHOD (A)

Dimethyl sulfate (30 g, 0.22 mole) is added to a stirred solution of 5-chloro-1-methyl-5-phenylpyrazole (39.5 g, 0.2 mole) in dry xylene (350 ml) and the reaction mixture is warmed to 105°C. to 115°C. for 18 hours. A brown syrup separates out, the reaction is cooled and the xylene is decanted off. Dry acetone (300 ml) is added and after stirring a white precipitate separates out and is filtered off, mp 100°C. to 102°C. 33.8 g, (55%). Recrystallization from dry acetone-toluene (1:1) gives white needles mp 102°C. to 104°C.

Analysis calculated for $C_{12}H_{15}N_2ClSO_4$: C, 45.22; H, 4.74; N, 8.79; Cl, 11.13. Found: C, 45.31; H, 4.81; N, 8.93; Cl, 11.24.

METHOD (B)

To a solution of dimethyl sulfate (1,596 g, 12.66 moles) at 70°C. to 74°C. is added 5-chloro-1-methyl-3-phenylpyrazole (1,523 g, 7.912 moles). During the exothermic addition the heat source is removed. After the exothermic reaction has ceased the reaction mixture is maintained at 80°C. by external heating for 2 hours and then is poured into toluene. Toluene is decanted off, leaving a residual syrup, which is treated with additional toluene and decanted off as above. The syrup is dissolved in chloroform, filtered, and the filtrate evaporated to an oil, which crystallizes from acetone to yield 1.52 kg, (60.3%) mp 95°C. to 96°C.

EXAMPLE 6

Preparation of 3-chloro-1,2-dimethyl-5-phenylpyrazolium iodide

To an aqueous solution of 1,2-dimethyl-3-chloro-5-phenylpyrazolium methyl sulfate is added a saturated aqueous solution of sodium iodide at 5°C. A copious precipitate is formed and filtered off. The solid is dissolved in methylene chloride and precipitated with diethyl ether to yield almost white crystals mp 162°C. to 164°C.

Analysis calculated for $C_{11}H_{12}N_2ClI$: C, 39.49; H, 3.62; N, 8.38; Cl, 10.64; I, 37.93. Found: C, 39.46; H, 3.61; N, 8.44; Cl, 10.47; I, 37.85.

EXAMPLE 7

Preparation of 3-cyclohexyl-1-methyl-2-pyrazolin-5-one

To ethyl 3-oxo-cyclohexanepropionic acid (4.4 g, 0.234 mole) in n-propanol (500 ml) is added dropwise with stirring under nitrogen at 80°C. methylhydrazine (13.8 g, 0.3 mole). After heating at reflux during 5 hours, the reaction is cooled and evaporated to a residual oil. Crystallization from ethylacetate gives a white powder mp 170.5°C. to 172°C.

Analysis calculated for $C_{10}H_{10}N_2O$; C, 66.63 H, 8.95; N, 15.54. Found: C, 66.59; H, 9.07; N, 15.69.

EXAMPLE 8

Preparation of 5-chloro-3-cyclohexyl-1-methylpyrazole

Phosphorus oxychloride (15.3 g, 0.1 mole) is added to 3-cyclohexyl-1-methyl-2-pyrazolin-5-one and the mixture stirred and heated at 120°C. to 135°C. for 8 hours. The cooled reaction mixture is then poured into ice-water, made alkaline with 1% aqueous sodium hydroxide and extracted with methylene chloride. Removal of solvent under reduced pressure, then in vacuo at 70°C. affords an oil, 8 g, (93.8%).

Analysis calculated for $C_{10}H_{15}N_2Cl$; C, 60.45; H, 7.61; N, 14.10; Cl, 17.85. Found: C, 60.28; H, 7.55; N, 14.20; Cl, 17.79.

EXAMPLE 9

Preparation of 3-chloro-5-cyclohexyl-1,2-dimethylpyrazolium methyl sulfate [and hydrogen sulfate (1:1)]

A mixture of 5-chloro-3-cyclohexyl-1-methylpyrazole (7 g, .0352 mole) and dimethyl sulfate (8.82 g, 0.07 mole) is heated to 80°C. and the heating source then removed. The reaction temperature rises to 88°C. and then, after the exotherm, the temperature is maintained at 80°C. by external heating for 6 hours. Toluene (100 ml) is added to the cooled reaction and the mixture is set aside overnight at room temperature and then a waxy solid is filtered off. Crystallization from methylene chloride-ether affords a granular product, mp 70°C. to 73.5°C., 11.2 g (100%). NMR and infrared spectra indicate a mixture of $CH_3SO_4$ and $HSO_4$ anions.

Analysis calculated for $C_{12}H_{21}N_2ClSO_4$ (as $CH_3SO_4$): C,44.36; H, 6.57; N, 8.63; S, 9.87; Cl, 10.92. Found C, 41.34; H, 6.24; N, 8.14; S, 9.12; Cl, 10.31.

A portion of the above compound is readily converted to the perchlorate whose melting point ranges from 216°C. to 218°C.

EXAMPLE 10

Preparation of 3,4,5-Tribromo-1-methylpyrazole

To 3,4,5-tribromopyrazole (4.5 g, 0.15 mole) in 3N aqueous sodium hydroxide (6 g, 0.15 mole) is added at room temperature with stirring dimethyl sulfate (19 g, 0.15 mole). After 10 minutes a solid separates out. An additional gram of dimethyl sulfate is added and the mixture is stirred for 3 days, filtered and the precipitate water washed and air dried to yield 33 g (73%), mp 85°C. to 86°C. Crystallization from cyclohexane yields desired solid product whose melting point ranges from about 90°C. to 91°C.

'Analysis calculated for C₄H₃N₂Br₃: C, 15.07; H, 0.95; N, 8.79; Br, 75.21. Found: C, 15.16; H, 0.82; N, 8.7; Br, 75.36.

EXAMPLE 11

Preparation of 3,4,5-tribromo-1,2-dimethylpyrazolium methyl sulfate (and perchlorate)

A stirred suspension of 1-methyl-3,4,5-tribromopyrazole (19.3 g, 0.06 mole) in dimethyl sulfate (80 ml) is stirred and heated at 130°C. to 135°C. for 6 hours. On cooling and setting aside overnight, a solid is obtained and filtered off, benzene washed and air dried to yield 18.7 g, (70%) whose melting point ranges from 199°C. to 203°C.

Analysis calculated for C₆H₉N₂Br₃SO₄: C, 16.19; H, 2.04; N, 6.29; Br, 53.88; S, 7.20. Found: C, 16.19; H, 1.99; N, 6.38; Br, 53.98; S, 7.31.

Treatment of the above methyl sulfate compound with aqueous perchloric acid affords the perchlorate whose melting point ranges from 300°C. to 300.5°C.

EXAMPLE 12

Preparation of 1,2-dimethyl-3-phenyl-5-piperidinopyrazolium iodide and perchlorate Piperidine (2.56 g, 0.03 mole) is added to 1,2-dimethyl-3-chloro-5-phenylpyrazolium methyl sulfate (4.77 g, 0.015 mole) in absolute ethanol (30 ml) and the mixture stirred with a bar magnet and heated under reflux for 4 hours. After cooling, the reaction mixture is evaporated under reduced pressure to a brown oil, and then dissolved in 50 ml of aqueous saturated sodium bicarbonate solution. The aqueous layer is extracted with ether and this organic layer discarded, then with chloroform (3×100 ml). Evaporation of the chloroform layer affords 1,2-dimethyl-3-phenyl-5-piperidinopyrazolium methyl sulfate as a viscous oil. The oil is redissolved in water and saturated aqueous potassium iodide solution is added. (Sodium iodide is also equally effective). An immediate copious white precipitate of 1,2-dimethyl-3-phenyl-5-piperidinopyrazolium iodide is formed, then filtered and washed with ice cold water to give 3.37 g, (56%) of product mp 179°C to 180°C. The melting point is unchanged by dissolving in chloroform, filtering and re-precipitating with diethyl ether and filtering off the solid. For analysis see Table I, compound 1.

Treatment of a portion of the iodide dissolved in warm water with 10% aqueous perchloric acid gives a white solid which after cooling to 10°C is filtered off, mp 137°C to 138°C; see compound 2, Table I. This material is also obtained directly by treating an aqueous solution of the methyl sulfate (above) with 10% sodium perchlorate and filtering off the product.

EXAMPLE 13

Preparation of 1,2-Dimethyl-3,5-dipiperidinopyrazolium bromide

4-Bromo-1,2-dimethyl-3,5-dipiperidinopyrazolium bromide (6.3 g, 0.015 mole) is dissolved in methanol (150 ml) and sodium hydroxide (1.2 g, 0.3 mole) and treated with 10% palladium on carbon. The mixture is hydrogenated at 25°C and absorbs hydrogen (290 ml) uncorrected (86%) in 25 minutes. The catalyst is filtered off, washed with ethanol and aqueous hydrogen bromide (10 ml) is added. The mixture is evaporated in vacuo to an oil, which is dissolved in chloroform and precipitated with diethyl ether to give a white powder on filtration mp 211°C. to 212°C, 3.4 g, (69%). Analysis see compound 10, Table IV.

A small amount of the bromide is dissolved in water and converted with 10% perchloric acid in quantitative yield to the perchlorate mp 171°C to 172°C, compound 11, Table IV.

EXAMPLE 14

Following the procedure of Method A or Method B above, there are obtained the compounds identified in Table IV in good yields and purity.

Table IV

Preparation of 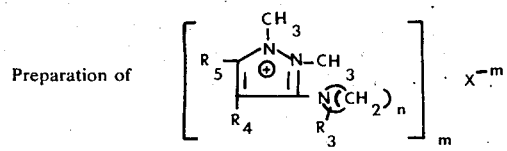

| No. | N(CH₂)ₙR₃ | X | R₄ | R₅ | Method | (%) Yield | (°C) mp | Analysis Calculated | | % Found | |
|-----|-----------|---|----|----|--------|-----------|---------|---------------------|---|---------|---|
| 1 | N⟩ | I⁻ | H | ⟨phenyl⟩ | A; A salt(NaI on intermediate (CH₃SO₄)) | 56 | 179–180 | C<br>H<br>N | 30.14<br>5.80<br>10.96 | C<br>H<br>N | 49.74<br>5.61<br>10.91 |
| 2 | N⟩ | ClO₄⁻ | H | ⟨phenyl⟩ | A; A acid(HClO₄ on intermediate (CH₃SO₄)) | 95 | 137–138 | C<br>H<br>N | 54.01<br>6.23<br>11.80 | C<br>H<br>N | 53.80<br>6.07<br>11.71 |
| 3 | N⟩ | CH₃SO₄⁻ | H | ⟨phenyl⟩ | A | 63 | 112–114 | C<br>H<br>N | 55.57<br>6.86<br>11.44 | C<br>H<br>N | 55.14<br>6.70<br>12.17 |
| 4 | N⟩ | I⁻ | H | ⟨phenyl⟩ | A | 75 | 122–124.5 | C<br>H<br>N | 51.40<br>6.09<br>10.58 | C<br>H<br>N | 51.39<br>6.23<br>10.38 |
| 5 | N⟩-CH₃ | I⁻ | H | ⟨phenyl⟩ | A | 45 | 184.5–185 | C<br>H<br>N | 51.40<br>6.09<br>10.58 | C<br>H<br>N | 51.30<br>6.07<br>10.55 |

Table IV-continued

Preparation of $\left[ R_5 \underset{R_4}{\overset{CH_3}{\underset{\oplus}{N-N-CH_3}}} \underset{R_3}{N(CH_2)_n} \right]_m X^{-m}$

| No. | N(CH$_2$)$_n$ / R$_3$ | X | R$_4$ | R$_5$ | Method | (%) Yield | (°C) mp | Analysis Calculated | | % Found | |
|---|---|---|---|---|---|---|---|---|---|---|---|
| 6 | N-piperidine, CH$_3$ | I$^-$ | H | phenyl | A | 51 | 151–152 | C | 51.40 | C | 51.07 |
| | | | | | | | | H | 6.09 | H | 6.13 |
| | | | | | | | | N | 10.56 | N | 10.74 |
| 7 | N-piperidine, CH$_3$ | I$^-$ | H | phenyl | A | 51 | 143–144.5 | C | 51.40 | C | 50.38 |
| | | | | | | | | H | 6.09 | H | 6.08 |
| | | | | | | | | N | 10.58 | N | 10.54 |
| 8 | N-piperidine | Br$^-$ | Br | N-piperidine | B | 88 | 170–170.5 | C | 42.67 | C | 42.77 |
| | | | | | | | | H | 6.21 | H | 45.98 |
| | | | | | | | | N | 13.27 | N | 13.28 |
| | | | | | | | | Br | 37.85 | Br | 37.93 |
| 9 | N-piperidine | ClO$_4^-$ | Br | N-piperidine | B Acid(HClO$_4$ on Br$^-$) | — | 154–155 | C | 40.77 | C | 40.79 |
| | | | | | | | | H | 5.93 | H | 6.01 |
| | | | | | | | | N | 12.68 | N | 12.77 |
| | | | | | | | | Br | 18.09 | Br | 18.14 |
| 10 | N-piperidine | Br$^-$ | H | N-piperidine | B Hydrogenration Pd/C/H$_2$/NaOH on Compound 9 | 69 | 211–212 | C | 52.48 | C | 52.33 |
| | | | | | | | | H | 7.93 | H | 7.66 |
| | | | | | | | | N | 16.32 | N | 16.04 |
| | | | | | | | | Br | 23.28 | Br | 22.64 |
| 11 | N-piperidine | ClO$_4^-$ | H | N-piperidine | B HClO$_4$ on compound 10 | 95 | 170–171 | C | 49.64 | C | 49.38 |
| | | | | | | | | H | 7.50 | H | 7.68 |
| | | | | | | | | N | 15.44 | N | 15.08 |
| 12 | N-piperidine, CH$_3$ | ClO$_4^-$ | H | phenyl | A Acid(HClO$_4$ on compound 14 the CH$_3$SO$_4^-$) | 54 | 110–112 | C | 55.21 | C | 54.01 |
| | | | | | | | | H | 6.54 | H | 6.51 |
| | | | | | | | | N | 11.36 | N | 10.92 |
| 13 | N-piperidine, CH$_3$ | Br$^-$ | H | phenyl | A Acid(HBr on compound 14 the CH$_3$SO$_4^-$) | 60 | 144–146 | C | 58.28 | C | 57.92 |
| | | | | | | | | H | 6.91 | H | 6.77 |
| | | | | | | | | N | 11.99 | N | 11.89 |
| 14 | N-piperidine, CH$_3$ | CH$_3$SO$_4^-$ | H | phenyl | A | 67 | glass | C | 56.68 | C | 56.39 |
| | | | | | | | | H | 7.14 | H | 7.15 |
| | | | | | | | | N | 11.02 | N | 11.20 |
| 15 | N-piperidine, CH$_3$ | Cl$^-$·2H$_2$O | H | phenyl | Ion exchange on Dowex 1-X8-Cl anion, using compound 14, CH$_3$SO$_4^-$ | 13 / 47 | 70.5–72 | C | 59.90 | C | 60.64 |
| | | | | | | | | H | 8.66 | H | 8.11 |
| | | | | | | | | N | 11.67 | N | 12.58 |
| | | | | | | | | Cl | 11.61 | Cl | 10.21 |
| 16 | N-piperidine, CH$_3$ | CH$_3$SO$_4^-$ | H | phenyl | A | 67 | glass | C | 56.68 | C | 55.07 |
| | | | | | | | | H | 7.14 | H | 7.09 |
| | | | | | | | | N | 11.02 | N | 10.60 |
| 17 | N-piperidine, CH$_3$ | Cl$^-$ | H | phenyl | Ion exchange on Dowex 1-X8-Cl anion using compound 16 | 60 | oil | N | 12.27 | N | 11.70 |
| | | | | | | | | Cl | 20.72 | Cl | 19.92 |
| 18 | N-piperidine, CH$_3$ | ClO$_4^-$ | H | phenyl | A Salt NaClO$_4$ on compound 16 | — | 94–95 | C | 55.21 | C | 54.94 |
| | | | | | | | | H | 6.54 | H | 6.48 |
| | | | | | | | | N | 11.36 | N | 11.38 |

Table IV-continued

Preparation of 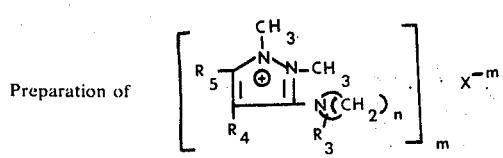

| No. | N(CH$_2$)$_n$ R$_3$ | X | R$_4$ | R$_5$ | Method | (%) Yield | (°C) mp | Analysis Calculated | | % Found | |
|---|---|---|---|---|---|---|---|---|---|---|---|
| 19 | N-piperidinyl, CH$_3$ | CH$_3$SO$_4^-$ Cl$^-$ (75:25) | H | phenyl | A | 98 | glass | C* | 55.78 | C | 51.91 |
| | | | | | | | | H* | 8.58 | H | 8.16 |
| | | | | | | | | N* | 10.84 | N | 10.38 |
| | | | | | | | | S* | 8.27 | S | 6.83 |
| | | | | | | | | Cl | — | Cl | 2.56 |
| 20 | N-piperidinyl, CH$_3$ | I$^-$ | H | phenyl | A Salt.NaI on compound 19 | — | glass | C | 50.62 | C | 50.59 |
| | | | | | | | | H | 7.50 | H | 7.89 |
| | | | | | | | | N | 10.42 | N | 10.42 |
| | | | | | | | | I | 31.47 | I | 30.60 |
| 21 | N-piperidinyl | I$^-$ | H | phenyl | A Salt.NaI on CH$_3$SO$_4^-$ salt | — | 99–100 | C | 49.39 | C | 47.99 |
| | | | | | | | | H | 7.25 | H | 7.24 |
| | | | | | | | | N | 10.80 | N | 10.42 |
| | | | | | | | | I | 32.60 | I | 31.61 |
| 22 | N-piperidinyl, CH$_3$ | I$^-$ | Br | phenyl | A | 75 | 193–194 | C | 42.87 | C | 42.81 |
| | | | | | | | | H | 4.87 | H | 4.33 |
| | | | | | | | | N | 8.82 | N | 8.82 |
| | | | | | | | | Br | 16.78 | Br | 16.90 |
| | | | | | | | | I | 26.65 | I | 26.68 |
| 23 | N-piperidinyl-CH$_3$ | I$^-$ | Br | phenyl | A | 63 | 211–213 | C | 42.87 | C | 42.58 |
| | | | | | | | | H | 4.87 | H | 5.00 |
| | | | | | | | | N | 8.82 | N | 8.78 |
| | | | | | | | | Br | 16.78 | Br | 16.89 |
| | | | | | | | | I | 26.65 | I | 26.56 |
| 24 | N-piperidinyl, CH$_3$ | ClO$_4^-$ | Br | phenyl | A | 6 | 197–199 | N | 9.20 | N | 8.91 |
| 25 | N-piperidinyl | I$^-$ | Br | phenyl | A | 16 | 201–202 | C | 41.58 | C | 39.15 |
| | | | | | | | | H | 4.58 | H | 4.38 |
| | | | | | | | | N | 9.09 | N | 8.66 |
| | | | | | | | | Br | 17.29 | Br | 16.30 |

*[as CH$_3$SO$_4$]

I claim:

1. A method for protecting plants from attack by fungi comprising: applying to said plants a fungicidally effective amount of a compound having a formula selected from the group consisting of:

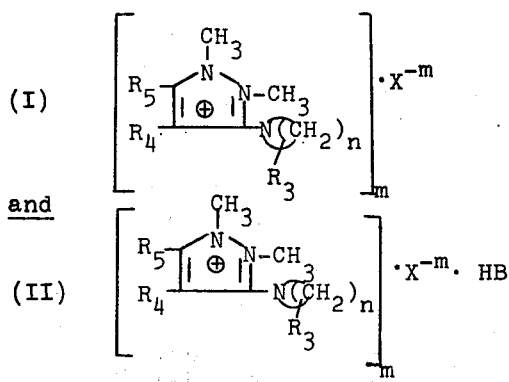

wherein R$_3$ represents a member selected from the group consisting of hydrogen, methyl, hydroxy and phenyl; R$_4$ represents a member selected from the group consisting of hydrogen, and halogen; R$_5$ represents a member selected from the group consisting of phenyl, cyclohexyl and $$-\underset{R_3}{N(CH_2)_n};$$

X represents an anion with a charge of 1 or 2; $n$ is five; $m$ represents an integer selected from 1 and 2; and HB is an acid of sufficient strength to form a stable salt with the —N(CH$_2$)$_n$ group.

2. The method according to claim 1 wherein said compound is a formula (I) pyrazolium salt and the plants to be protected are cereal grain plants.

3. The method according to claim 1 wherein the fungus organism is powdery mildew and the compound is applied in liquid form as a spray containing 100 ppm to 5600 ppm of the formula (I) pyrazolium salt compound.

4. The method according to claim 1 wherein said compound is: 1,2-dimethyl-3-phenyl-5-piperidinopyrazolium iodide, hydroiodide.

5. The method according to claim 1 wherein the compound is: 1,2-dimethyl-3-phenyl-5-piperidinopyrazolium perchlorate, perchloric acid salt.

6. The method according to claim 1 wherein the compound is: 1,2-dimethyl-3-(4-methylpiperidino)-5-phenylpyrazolium iodide.

7. The method according to claim 1 wherein the compound is: 4-bromo-1,2-dimethyl-3,5-dipiperidinopyrazolium bromide, hydrobromide.

8. The method according to claim 1 wherein the compound is: 1,2-dimethyl-3,5-dipiperidinopyrazolium perchlorate.

9. The method according to claim 1 wherein the compound is: 1,2-dimethyl-3-(3-methylpiperidino)-5-phenylpyrazolium perchlorate.

10. A method for controlling fungi by contacting said fungi with a fungicidally effect amount of a compound according to claim 1 having a formula selected from the group consisting of:

I and (II)

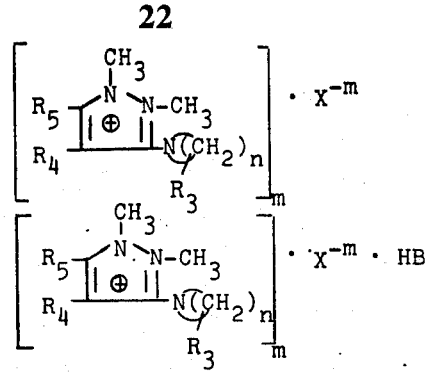

wherein $R_3$ represents a member selected from the group consisting of hydrogen, methyl, hydroxy and phenyl; $R_4$ represents a member selected from the group consisting of hydrogen, and halogen; $R_5$ represents a member selected from the group consisting of phenyl, cyclohexyl and

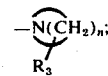

X represents an anion with a charge of 1 or 2; $n$ is five; $m$ represents an integer selected from 1 and 2; and HB is an acid of sufficient strength to form a stable salt with the

group.

11. A method according to claim 10 wherein the fungus organism is powdery mildew and the compound is applied in liquid form as a spray containing 100 ppm to 5600 ppm of the formula (I) pyrazolium salt compound.

* * * * *